United States Patent [19]

Ornstein et al.

[11] Patent Number: 4,575,490

[45] Date of Patent: Mar. 11, 1986

[54] ONE STEP METHOD FOR SPHERING AND FIXING WHOLE BLOOD ERYTHROCYTES

[75] Inventors: Leonard Ornstein, White Plains; Young R. Kim, Hartsdale, both of N.Y.

[73] Assignee: Technicon Instruments Corporation, Tarrytown, N.Y.

[21] Appl. No.: 584,882

[22] Filed: Feb. 29, 1984

[51] Int. Cl.⁴ .................... G01N 21/49; G01N 33/49; G01N 15/14
[52] U.S. Cl. ........................................ 436/63; 356/39; 424/3; 436/10; 436/17
[58] Field of Search ...................... 252/408.1; 356/39; 424/2, 3, 101; 436/10, 16–18, 63, 164, 166

[56] References Cited

U.S. PATENT DOCUMENTS 4,389,490 6/1983 Crews et al. .................... 436/17
4,412,004 10/1983 Ornstein et al. .................... 436/10

OTHER PUBLICATIONS

Potentiation and Stabilization of Glutaraldehyde Biocidal Activity Utilizing Surfactant-Divalent Cation Combinations, Gorman et al, Intl. J. of Pharmaceutics, 4(1979) 57–65.
Chemical Abstract 77(21):135620n.

Primary Examiner—Arnold Turk
Attorney, Agent, or Firm—Morgan, Finnegan, Pine, Foley & Lee

[57] ABSTRACT

A rapid one step, one reagent method is disclosed for the isovolumetric sphering and fixing of whole blood erythrocytes.

20 Claims, No Drawings

ONE STEP METHOD FOR SPHERING AND FIXING WHOLE BLOOD ERYTHROCYTES

BACKGROUND OF THE INVENTION

This invention relates generally to a rapid one-reagent method for sample preparation for improved electrooptical methods for measuring human and animal erythrocyte volumes and cell hemoglobin contents. More particularly, it relates to a one step method for treating mammalian red blood cells in a sample which can be effectively measured electrooptically for determination of red blood cell volumes whereby the one-step, single reagent treatment provides isovolumetric sphering of erythrocytes in the sample independent of erythrocyte concentration in the original blood sample and without inducing lysis.

Prior art methods utilizing the measured amount of light scattered from individual red cells (erythrocytes) to determine the individual and mean volumes of red cells were subject to error for two reasons: since the native human red cell is a biconcave disc, the amount of light scattered will vary with the orientation of the cell with respect to the incident light beam; and, the shape of the cells can change during dilution and pumping steps.

For a discussion of the above, see Hemolysis and Related Phenomena, Chapter II, pp 10–49 by Eric Ponder (1948) and Transformation and Restoration of Biconcave Shape of Human Erythrocytes Induced by Amphilic Agents and Changes of Ionic Environment, Biochemica et Biophy. Acta, Bernard Deuticke, pp 494–500 (1968).

In Ornstein et al U.S. Pat. No. 4,412,004, commonly assigned, a method is disclosed and claimed which eliminates both of the above-described causes of error and permits a vastly improved method for determination of human red blood cell volumes. In the '004 patent, the inventive method involves a two-step procedure of first sphering erythrocytes isovolumetrically and then fixing isotonically. The method was devised as a two-step procedure in order to be assured that sphering had reached completion before the fixing process began, otherwise, cells might become "stiffened" by cross-linking which occurs during fixation and thus became "frozen" in some intermediate shape between the native biconcave shape and the desired spherical shape. Fixing immediately after sphering permitted the use of higher sphering agent/protein ratios in the fixing solution because cells which might otherwise lyse, were fixed before that could happen. This leads to a more convenient implementation for automated clinical use.

It has now been found, quite unexpectedly, that a single reagent containing appropriate and limited ranges of concentrations of both sphering agent and fixing agent can achieve complete isovolumetric sphering of all erythrocytes of a large range of clinical samples of blood, independently of the concentration of erythrocytes in the whole blood sample, and without inducing lysis of any of the erythrocytes in any of the diluted blood samples. It was not obvious to one of ordinary skill in the art that the employment of particular parameters in a one-step method as disclosed and claimed herein could allow for a procedure in which the speed of the sphering step remains sufficiently greater than the fixing process so that the cells are completely sphered before they have appreciably stiffened. This leads to a faster and still more convenient implementation for automated clinical use.

SUMMARY OF THE INVENTION

In accordance with this invention, there is claimed an improved, one step diagnostic method for treating mammalian red blood cells in a sample which can be effectively measured electrooptically for determination of red blood cell volumes which comprises treating an anticoagulated whole blood sample with a single aqueous sphering agent/fixing agent reagent at a temperature in the range of 4° C. to 37° C. over a reaction period of up to 180 seconds employing a whole blood dilution factor of from 1:300 to 1:4,000, wherein said one-step, single reagent treatment provides isovolumetric sphering of the erythrocytes in the sample independent of the concentration of said erythrocytes in the whole blood sample and without inducing lysis of said erythrocytes in the resulting diluted sample.

In one preferred embodiment, the concentration of sphering agent in the reagent is from about 0.5 mg % to about 3.0 mg %, preferably where it does not exceed 2.0 mg %, and most preferred is a concentration of about 1 mg %.

In another embodiment and in accordance with this invention, the sphering agent employed is an alkali metal salt of an alkyl sulfate, e.g. sodium dodecyl sulfate. It is understood however that any suitable sphering agent known in this technology is applicable.

In another embodiment and in accordance with this invention, the fixing agent, e.g. glutaraldehyde, is provided at a concentration of from about 0.05% to about 0.3%, preferably at about 0.2%. For the purposes of this invention glutaraldehyde is preferred; however, other aldehydes, such as formaldehyde and other fixing agents known in this technology are employable.

In another embodiment and in accordance with this invention, a phosphate buffer is included in the aqueous reagent, preferably at a concentration adjusted to provide a reagent pH of from 6.0 to 7.5, and more preferably, at a concentration of about 0.035M to provide a reagent pH of about 7.3.

In another embodiment and in accordance with this invention, sodium chloride is added to the aqueous reagent, preferably at a concentration adjusted to provide a reagent osmolarity to about 290 mOs/kg.

In another embodiment and in accordance with this invention, the diagnostic method is effected at about 25° C. over a period of about 60 seconds and at a whole blood dilution factor in the range 1:600 to 1:700.

In further accordance with this invention, there is claimed a composition for sphering red blood cells in an anticoagulated whole blood sample in a single step to provide isovolumetric sphering independent of the red blood cell concentration in the whole blood sample and without lysis inducement which comprises an aqueous sphering agent/fixing agent reagent comprising from about 0.5 mg % to about 3.0 mg % (mg/100 ml) of a sphering agent and from about 0.05% to about 0.3% (w/w%) of a fixing agent).

DETAILED DESCRIPTION OF THE INVENTION

The herein disclosed and claimed invention relates to a one step method for the isovolumetric sphering and fixing of whole blood erythrocytes. It is a significant improvement over prior art methods with regard to its kinetics and its ability to be adapted to an automated system. It allows for the production of single formulations of reagents which completely and isovolumetrically sphere all erythrocytes of a large range of clinical samples of blood, independently of the concentration of erythrocytes in the blood samples, and without inducing lysis of any of the erythrocytes in any of the diluted blood samples.

It has been found, unexpectedly, that conditions can be employed, such that, when whole blood is added to, and rapidly and thoroughly mixed with a single reagent containing appropriate and limited ranges of concentrations of both sphering agent and fixing agent, complete isovolumetric sphering of all erythrocytes of a large range of clinical samples of blood can be achieved without inducing lysis of any of the erythrocytes in any of the diluted blood samples. That such is achievable resides in the utilization of concentrations and temperatures which permit a particular reaction kinetics—the rate of sphering remains sufficiently greater than the rate of fixing so that the cells are completely sphered before they have stiffened appreciably.

A preferred set of conditions for the instant invention is set forth hereinbelow:
Temperature: room temperature (25° C.±8° C.)
Whole blood dilution factor: 600±100
Reaction time: 60 seconds±40 seconds
Reagent formulation:
  sodium dodecyl sulfate: 1 mg %±0.2 mg %
  glutaraldehyde: 0.2%±0.1%
  phosphate buffer: 0.035±0.015M at pH; 7.3±0.2
  sodium chloride: to adjust reagent osmolarity to 290±5 mOs/kg When a whole blood sample is mixed with the above reagent, red cells are isovolumetrically sphered for more accurate and precise cell volume and hemoglobin measurements by a light scattering flow cytometer. A preferred flow cytometer for the measurement uses a HeNe red laser (wavelength 632.8 nm) as the light source, and the illuminated field is defined as a 20 $\mu m \times 100$ $\mu m$ slit imaged in the center of the sheathed flow cell. Two optical light scatter measurements are taken, the low (2° to 3°) angle signals and high (5° to 15°) angle signals.

The low angle signals and the high angle signals are paired to form a $50 \times 50$ erythrocyte volume and hemoglobin cytogram (the other high angle signals can be used to generate the platelet histogram). The cytogram's data are processed by coincidence trimming followed by a non-linear two-dimensional transformation. A computer program transfers the scatter amplitude signals into erythrocyte volume and hemoglobin concentration histograms as disclosed in commonly assigned U.S. patent application Ser. No. 547,513, filed Oct. 31, 1983.

The following parameters can be generated from the cell preparation:
1. Red blood cell count: (RBC)
2. Mean corpuscular volume: (MCV)
3. Cell hemoglobin concentration mean: (CHCM)
4. Hematocrit: (HCT)
5. Red cell volume distribution width: (RDW)
6. Hemoglobin distribution width: (HDW)
7. Platelets: (PBC)
8. Mean platelet volume: (MPV)
9. Plateletcrit: (PCT)
10. Platelet distribution width: (PDW)

Broader parameters applicable to the present invention are provided hereinbelow:

Reaction Temperatures: can be varied from 4° C. to 37° C. without risking any significant change in results. +0.37% at 4° C. and −0.62% at 37° C. in whole blood MCV were observed. No change occurred in RBC and Plt counts at either temperature.

Whole Blood Dilution Factor: can be varied from 1:300 to 1:4,000. Without risking any significant change in results. Less than +1% at 1:300 and less than −1% at 1:4,000 in fresh whole blood MCV has been observed.

Sphering Agent Concentration: can be varied from 0.5 mg % to 3.0 mg % when all test samples are fresh whole bloods. Aged blood samples are more prone to lysis at concentrations above 2.0 mg %.

Fixing Agent Concentrations: can be reduced to 0.05%. Above 0.3% interferes with uniform sphering and excessive cross-linking takes place before sphering of erythrocytes is complete.

pH of the Reagent: can range from 6.0 to 7.5. One pH unit beyond these limits produce −1.5% change in MCV and +1.5% in CHCM to whole blood.

Reaction Times: at 180 seconds results in less than 1% change in whole blood MCV and CHCM. Up to 300 seconds result in MCV's with less than −2% error and CHCM's with less than +2% error.

EXAMPLE

Reagent Formulation

Sodium Dodecyl Sulfate: 3 mg %
Glutaraldehyde: 0.1%
phosphate buffer: 0.02M
NaCl: To bring up to 290 mOSm/L

Instrument (1) Light Sources: HeNe red laser ($\lambda = 632.8$ nm)
(2) Illumination Field: 20 $\mu m \times 100$ $\mu m$ slit
(3) Sheathed Flow cell (Sheath fluid=phosphate buffered saline, 290 mOSm/L, pH 7.4
(4) Two Optical Light Scatter Measurements Angle:
  Low 2° to 3°
  High 5° to 15°
(5) Sample Stream Width: 15$\mu$

Procedure (1) 0.01 ml whole blood (EDTA anti-coagulated) sample is added to 6.0 ml of the reagent and mixed immediately. The red cells will be isovolumetrically sphered.
(2) Aspirate the sample of sphered and fixed red cells through the sample stream and take 40 second reading.

The low angle signals and the high angle signals at low gain are paired to form a $50 \times 50$ RBC cytogram. The other high angle signals ($\times 10$ low gain) is used to generate the platelet histogram. The cytogram's data is processed by coincidence trimming followed by a non-linear two dimensional transformation. A computer program transforms the scatter amplitude signals into RBC volume and a hemoglobin concentration histogram.

The system must be precalibrated using 10 normal bloods whose parameters are pre-determined by reference methods.

It should be understood by those skilled in the art that various modifications may be made in the present invention without departing from the spirit and scope thereof as described in the specification and defined in the appended claims.

What is claimed is:

1. A method for treating mammalian red blood cells in a whole blood sample which can be subsequently effectively measured electrooptically for determination of red blood cell volumes which comprises treating in a single step an anticoagulated whole blood sample with an isotonic reagent solution containing both a sphering agent and a fixing agent at a temperature in the range of 4° C. to 37° C. over a reaction period of up to 180 seconds employing a whole blood dilution factor of from 1:300 to 1:4,000, wherein said sphering agent and said fixing agent are present in the reagent at concentrations and at a ratio which provides isovolumetric sphering of the erythrocytes in the sample independent of the concentration of said erythrocytes in the whole blood sample and without inducing lysis of said erythrocytes in the resulting diluted sample.

2. The method of claim 1 wherein the concentration of said sphering agent in the reagent is from about 0.5 mg/100 ml to about 3.0 mg/100 ml.

3. The method of claim 2 wherein said concentration does not exceed 2.0 ml/100 ml.

4. The method of claim 3 wherein said concentration is about 1 mg/100 ml.

5. The method of claim 1 wherein said sphering agent is an alkali metal salt of an alkyl sulfate.

6. The method of claim 5 wherein said alkyl sulfate salt is sodium dodecyl sulfate.

7. The method of claim 1 wherein the concentration of said fixing agent is from about 0.05 w/w% to about 0.3 w/w%.

8. The method of claim 7 wherein said concentration is about 0.2 w/w%.

9. The method of claim 1 wherein said fixing agent is glutaraldehyde.

10. The method of claim 1 wherein said aqueous reagent includes a phosphate buffer.

11. The method of claim 10 wherein the phosphate buffer is adjusted to provide a reagent pH of from 6.0 to 7.5.

12. The method of claim 11 wherein said phosphate buffer concentration is about 0.035M and provides a reagent pH of about 7.3.

13. The method of claim 1 wherein said aqueous reagent includes sodium chloride.

14. The method of claim 13 wherein the sodium chloride concentration is adjusted to provide a reagent osmolarity to about 290 Os/kg.

15. The method of claim 1 wherein said temperature is maintained at about 25° C. (room temperature).

16. The method of claim 1 wherein said reaction period is about 60 seconds.

17. The method of claim 1 wherein said whole blood dilution factor is about 1:600 to 1:700.

18. The method of claim 1 wherein said aqueous reagent comprises sodium dodecyl sulfate at a concentration of about 1 mg %, glutaraldehyde at a concentration of about 0.2%, about pH 7.3 phosphate buffer at a concentration of about 0.035M and sodium chloride in an amount to provide a reagent osmolarity to about 290 mOs/kg.

19. The method of claim 1 wherein the resulting, diluted sample is subjected to light scattering measurement for determination of at least one of red blood cell volumes and cell hemoglobin content.

20. The method of claim 1 wherein the resulting, diluted sample is measured with a flow cytometer.

* * * * *